(12) United States Patent
Miller

(10) Patent No.: US 8,317,673 B2
(45) Date of Patent: Nov. 27, 2012

(54) DEVICE AND METHOD FOR CONTROLLING EMISSION OF RADIATION

(75) Inventor: Keith E. Miller, Germantown, TN (US)

(73) Assignee: Warsaw Othopedic, Inc., Warsaw, IN (US)

( * ) Notice: Subject to any disclaimer, the term of this patent is extended or adjusted under 35 U.S.C. 154(b) by 448 days.

(21) Appl. No.: 12/771,014

(22) Filed: Apr. 30, 2010

(65) Prior Publication Data

US 2011/0270012 A1    Nov. 3, 2011

(51) Int. Cl.
*A61N 5/00* (2006.01)
(52) U.S. Cl. .......................................... 600/3; 623/17.11
(58) Field of Classification Search .................. 600/1–8; 623/17.11; 128/897–899
See application file for complete search history.

(56) References Cited

U.S. PATENT DOCUMENTS

| | | | |
|---|---|---|---|
| 4,706,652 A | 11/1987 | Horowitz | |
| 5,562,594 A * | 10/1996 | Weeks | ............................... 600/3 |
| 6,120,540 A | 9/2000 | Apple | |
| 6,695,760 B1 | 2/2004 | Winkler et al. | |
| 6,749,555 B1 | 6/2004 | Winkler et al. | |
| 6,976,949 B2 | 12/2005 | Winkler et al. | |
| 7,182,726 B2 | 2/2007 | Williams | |
| 7,381,178 B2 | 6/2008 | Winkler et al. | |
| 7,407,476 B2 | 8/2008 | Lubock et al. | |
| 7,465,268 B2 | 12/2008 | Lubock et al. | |
| 7,497,819 B2 | 3/2009 | White et al. | |
| 7,497,820 B2 | 3/2009 | White et al. | |
| 7,662,082 B2 | 2/2010 | White et al. | |
| 2003/0233136 A1 | 12/2003 | Williams | |
| 2004/0167372 A1 | 8/2004 | Winkler | |
| 2005/0027157 A1 | 2/2005 | Winkler | |
| 2005/0131267 A1 | 6/2005 | Talmadge | |
| 2005/0131268 A1 | 6/2005 | Talmadge | |
| 2005/0131269 A1 | 6/2005 | Talmadge | |
| 2006/0047178 A1 | 3/2006 | Winkler et al. | |
| 2006/0100475 A1 | 5/2006 | White | |
| 2007/0142695 A1 | 6/2007 | White | |
| 2007/0167667 A1 | 7/2007 | Lubock et al. | |
| 2007/0167668 A1 | 7/2007 | White et al. | |
| 2009/0264696 A1 | 10/2009 | White et al. | |
| 2010/0137674 A1 * | 6/2010 | Evans et al. | ....................... 600/7 |

* cited by examiner

*Primary Examiner* — Charles A Marmor, II
*Assistant Examiner* — Shannon Canty

(57) ABSTRACT

Embodiments of the invention include a device for therapeutically delivering radiation to tissue. Some embodiments include a radiation source and a combination of members surrounding the radiation source that move relative to one another to permit or restrict the emitting of radiation from the device. Limits to the movement of the combination of members may be imposed by one or more biodegradable members.

20 Claims, 4 Drawing Sheets

DEVICE AND METHOD FOR CONTROLLING EMISSION OF RADIATION

FIELD OF THE INVENTION

The present invention relates generally to the field of delivering radiation to tissue, and more particularly relates to delivering radiation from an implantable device by allowing radiation to be emitted from the implantable device and then restricting radiation from being emitted from the implantable device after activation of a release or erosion of a biodegradable member.

BACKGROUND

An implant may be used as a delivery vehicle for radiation in various circumstances. An implant including a radiation source may have a structural or other function in addition to its radiation delivery function. For example, an implant including a radiation source may be used to respond to a spinal pathology and as part of a cancer treatment. Some implants may also have a radiation delivery function alone, such as brachytherapy devices. By way of further example, some implants may be interbody spinal implants or a vertebral body replacement implants. Implants classified as vertebral body replacement implants may include implants used in association with corpectomy or vertebrectomy procedures to stabilize spinal structures. Removal, or excision, of a vertebra may be referred to as a vertebrectomy. Excision of a generally anterior portion, or vertebral body, of the vertebra may be referred to as a corpectomy. If only a portion of a vertebral body and adjacent discs are removed and replaced, the procedure may be called a hemi-vertebrectomy. Any of these types of implants or other implants may include a suitable radiation source. It may be advantageous in some circumstances to provide a way of restricting or even stopping the emission of radiation from an implant that includes a radiation source. Some embodiments of an improved device may include the capability to emit a therapeutically effective amount of radiation for a period of time and then to reduce or shut off the radiation. Some embodiments of an improved device may be operable to reduce or shut off radiation emission without further surgical intervention.

SUMMARY

One embodiment of the invention is a device for therapeutically delivering radiation to tissue. The device may include a body having one or more areas comprising a material that substantially blocks the transmission of radiation, a radiation source located within the body and configured to deliver radiation, and a radiolucent area in the body. A closure mechanism made at least in part of a material that substantially blocks the transmission of radiation and that is configured to cover at least a portion of the radiolucent area may be included. Some embodiments include a biodegradable member coupled to the body and contacting the closure mechanism to prevent the closure mechanism from being moved to limit the radiolucent area and thereby restrict or prevent the therapeutic delivery of radiation.

An embodiment of the invention is a device for therapeutically delivering radiation to tissue. The device may include a radiation source, a radiation containment means comprising a material that substantially blocks the transmission of radiation, the radiation containment means for at least in part encapsulating the radiation source, and a radiolucent area in the radiation containment means. Some devices also include a shutter means for closing the radiolucent area. The shutter means may be made at least in part of a material that substantially blocks the transmission of radiation. The device may also include a release means coupled to the radiation containment means and contacting the shutter means. The release means may be configured to hold the shutter means in an open position to allow the delivery of therapeutically effective amounts of radiation until a degradation of the release means occurs. After a degeneration of the release means the shutter means is allowed to at least in part close and restrict the delivery of radiation.

Another embodiment of the invention is a method of therapeutically delivering radiation to tissue. The method embodiment may include providing a device with a body having one or more areas comprising a material that substantially blocks the transmission of radiation, and wherein the body includes a radiolucent area; providing a closure mechanism made at least in part of a material that substantially blocks the transmission of radiation, wherein the closure mechanism is configured to cover the radiolucent area; and providing a biodegradable member between the body and the closure mechanism to restrict movement of the closure mechanism relative to the body. The method embodiment may also include implanting the body, the closure mechanism, and the biodegradable member into or near tissue to which radiation will be delivered and irradiating the tissue by allowing radiation to be delivered from the body at least through the radiolucent area. The method embodiment may further include exposing the biodegradable member to bodily fluids, tissues, or cell reactions to weaken the biodegradable member and to permit the closure mechanism to move relative to the body in a direction that restricts the delivery of radiation.

DETAILED DESCRIPTION

Figure 1:
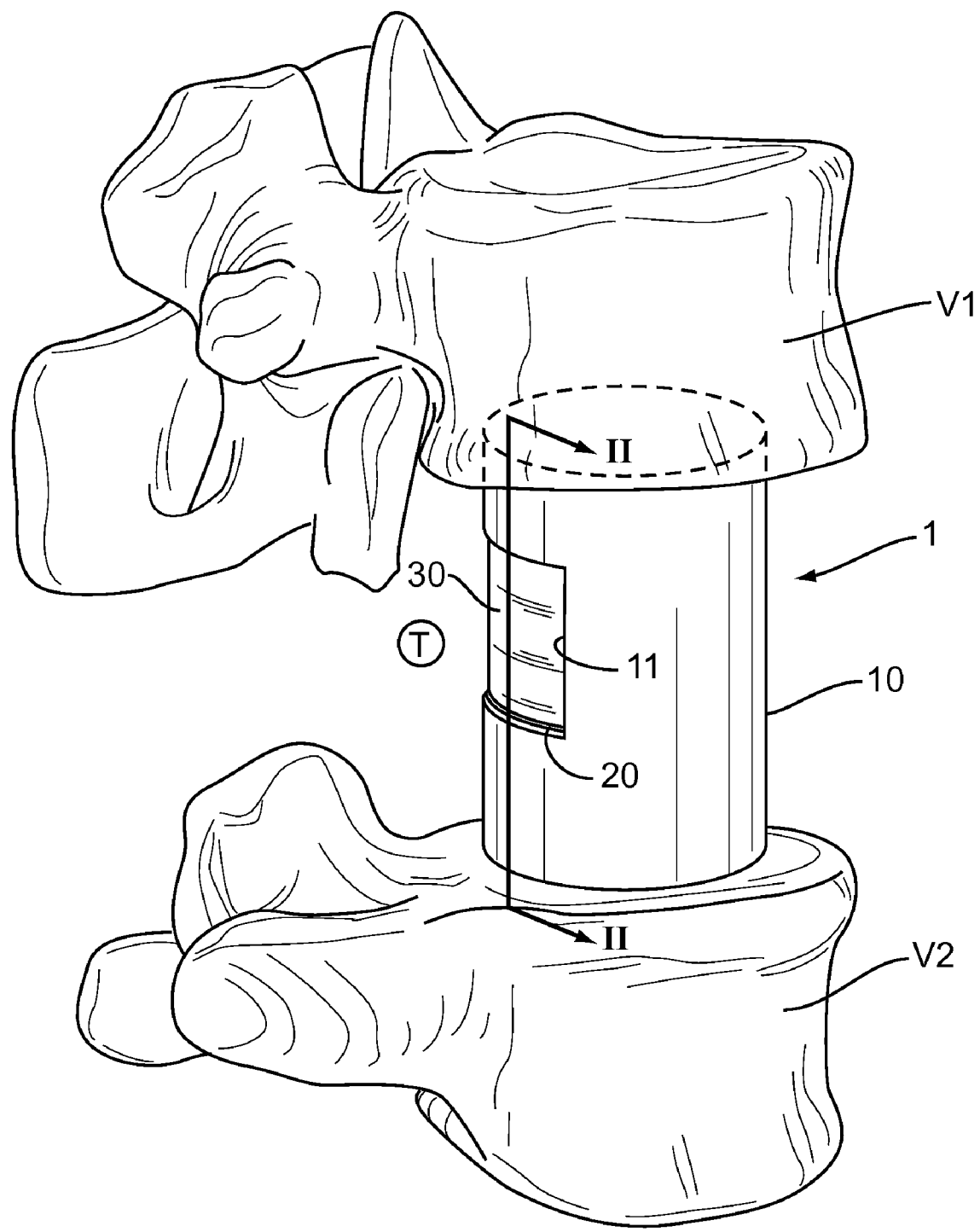
FIG. 1 is a perspective view of an embodiment of a device for therapeutically delivering radiation to tissue implanted between vertebrae.
Figure 2:
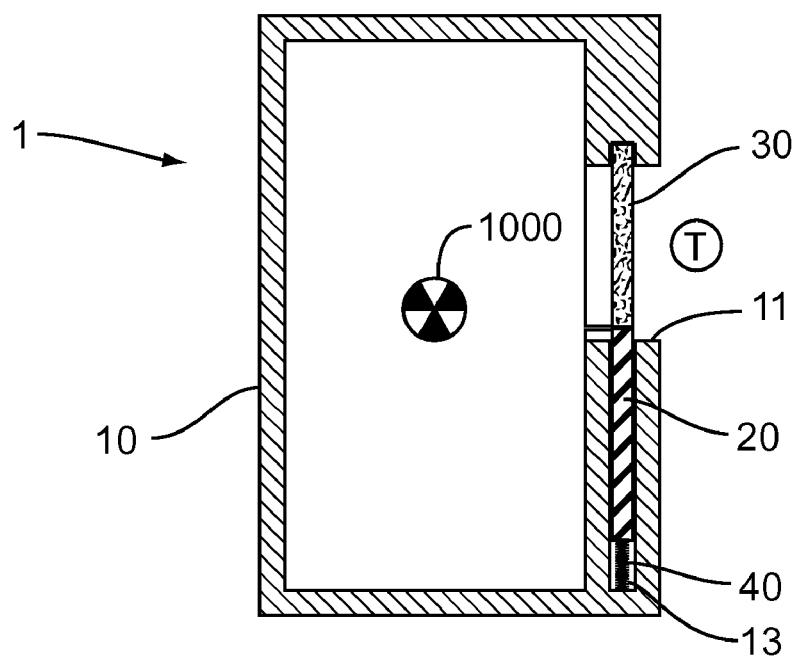
FIG. 2 is a cross-sectional view of the device of FIG. 1.
Figure 3:
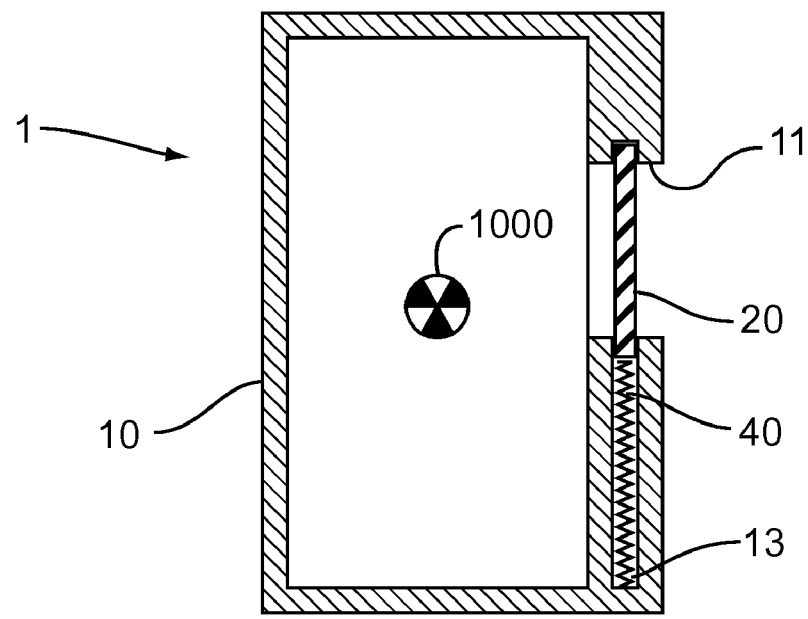
FIG. 3 is a similar cross-sectional view to the cross-sectional view of FIG. 2 in a different state of device component movement.

A device 1 for therapeutically delivering radiation to tissue is illustrated in FIGS. 1-3. The device 1 illustrated is a vertebral body replacement implant. However, in other embodiments, the device may be any implant that may be used in a space between two vertebrae, such as the illustrated first vertebra V1 and the second vertebra V2. Alternatively, the device may be a brachytherapy device or any other implantable device for delivering radiation. The lateral periphery of the device 1 is substantially round in cross-section. Other embodiments may have a periphery that is substantially the shape of an oval, kidney, triangle, rectangle, square, any polygonal or curved shape, or any combination of shapes. In some embodiments, a vertebral body replacement type device may be configured to expand from a first height of a second taller height. The device 1 or any of its component parts may be made from any biocompatible material.

The device 1 shown has a body 10 with one or more areas that in whole or in part includes a material that substantially blocks the transmission of radiation. Such a material for the body 10, or for any other components of the device 1, may include, but are not limited to, cobalt chrome, titanium, stainless steel, tantalum, niobium, gold, lead, barium, bismuth, tin, and tungsten. A radiation blocking material may be applied to the inside or outside or be encapsulated within a component so that only certain of the materials are in direct communication with tissues or fluids of a patient. A radiation blocking material may be applied to or integrated with a component by any effective mechanism, including but not limited to, chemically bonding, an intervening adhesive, welding, melting, press fitting, ion deposition, or mechanically locking. As used herein, the term "blocking the transmission of radiation" and similar terms mean that a material, composite, or component blocks the passage of therapeutically effective amounts of radiation from a radiation source. The blocking of radiation may not be complete such that there is no measurable amount of radiation allowed through a component.

The device 1 may also include a radiation source 1000, as illustrated in FIGS. 2 and 3, configured to deliver radiation in some embodiments. The radiation source 1000 is shown within the body 10. In other embodiments, a radiation source may be located at any effective location in or on a device. Radiation may be emitted in any or all directions from the radiation source 1000 in various embodiments. Although the radiation source 1000 is shown in approximately the middle of the body 10, the radiation source 1000 may be located anywhere or everywhere within the body 10 or the device 1. The radiation source 1000 may be of any size and located to approximately distribute radiation evenly out of any openings or other radiolucent areas of the device 1. The direction and pattern of radiation transmission may be altered by the shape, orientation, and placement of the radiation source 1000.

The radiation source 1000 may include any therapeutically effective radiation generating material or mechanism. Suitable radiation sources for use in various embodiments include both solids and liquids. By way of non-limiting example, the radiation source 1000 may be a radionuclide, such as I-125, I-131, Yb-169, Ir-192 or other radionuclides that emit photons, beta particles, gamma radiation, or other therapeutic energy or substances. The radioactive material may also be a fluid made from any solution of radionuclide(s), e.g., a solution of I-125 or I-131, or a radioactive mixture may be produced using a slurry of a suitable fluid containing small particles of solid radionuclides, such as Au-198, Y-90. Radionuclides may also be delivered in a gel. One radioactive material useful in some embodiments is Iotrex®, a nontoxic, water soluble, nonpyrogenic solution containing sodium 3-(125I)iodo-4-hydroxybenzenesulfonate (125I-HBS), available from Proxima Therapeutics, Inc. of Alpharetta, Ga. Radioactive micro spheres of the type available from the 3M Company of St. Paul, Minn., may also be used. A radioactive source of various embodiments may be preloaded into a device 1 at the time of manufacture, at some other time prior to a surgical procedure, or loaded after the device 1 has been implanted. By way of further non-limiting example, one or more solid radioactive micro spheres may be inserted through a catheter on a wire and into a device.

The body 10 may include a radiolucent area, such as the hole 11 illustrated in FIGS. 1-3. Radiolucent areas of other embodiments may include holes or openings of any size or configuration through material that would otherwise substantially block the transmission of radiation. In other embodiments, radiolucent areas may be any material or composite that allows a therapeutically effective amount of radiation to penetrate through an area of a body, whether or not a hole or opening is provided. For example, the hole 11 in the body 10 may be filled in or covered over with a radiolucent material. A cover may be applied to an inside or outside surface of the body 10. Such a combination of a hole and radiolucent material would provide a radiolucent area, as used herein. Portions of the body 10, other than the hole 11, shown in the illustrated embodiment are areas that include materials that substantially block the transmission of radiation. Radiolucent materials or composites of some embodiments may include polyetheretherketone (PEEK) or a PEEK composite, some metal alloys, various other polymers and composites, and bone or bone-based materials. For example and without limitation, bone or bone-based materials may include one or more of allograft, autograft, xenograft, and demineralized bone.

A closure mechanism 20 made at least in part of a material that substantially blocks the transmission of radiation is illustrated in FIGS. 1-3. The closure mechanism 20 shown is configured to cover at least a portion of the radiolucent area. Specifically as illustrated in FIG. 3, the closure mechanism 20 may cover the hole 11 that forms a radiolucent area through the body 10. In the illustrated example, radiation from the radiation emitting device 1000 is permitted to travel through the hole 11 and the biodegradable member 30 to deliver therapeutic dosages to a treatment site "T" depicted in FIG. 2. In FIG. 3, where the hole 11 is covered by the closure mechanism 20, radiation is not permitted to be delivered laterally from the device 1. The closure mechanism 20 shown in FIG. 2 is in a notch 13 in the body 10. The closure mechanism 20 has been moved from a majority of the notch 13 in the illustration of FIG. 3 to cover the hole 11. In some embodiments, the closure mechanism 20, or another closure mechanism, may cover only a part of the hole 11, or another hole, opening, or radiolucent area. In some embodiments, a closure mechanism may first cover part of a hole, opening, or radiolucent area after a first action, and may cover more or all of the hole, opening, or radiolucent area after a further action. Some embodiments may also include a closure mechanism that intermittently covers and uncovers various holes, openings, or radiolucent areas.

A biasing member 40 is illustrated in FIGS. 2 and 3. The biasing member 40 shown resides in the notch 13 in the body 10 and is disposed between the body 10 and the closure mechanism 20 to urge the closure mechanism upward, as illustrated, to restrict the delivery of radiation through the radiolucent area formed by the hole 11. The biasing member 40 illustrated is a coil spring, but in other embodiments could be any effective mechanism, including but not limited to, a leaf spring, a wave spring, a resilient block, a transverse coil spring, an expandable mechanism, or a tensioned device with a connected strand to pull the closure mechanism 20. A biasing member of some embodiments may also be any effective actuator, and may include one or more drive mechanisms and signal devices. Drive components may be housed within the device at any effective location. Example drive mechanisms include, but are not limited to, micromotors, magnetic drives, ratchet drives, piezoelectric drives, hydraulic actuators, and combinations of these drives. Signals to drive these mechanisms may be provided by wired or wireless transmission, physical attachment, hydraulic actuation, radio signal, or any other effective signal or mechanism for the drive mechanism selected.

The device 1 illustrated in FIGS. 1 and 2 also includes a biodegradable member 30 coupled to the body 10 and contacting the closure mechanism 20. In various embodiments, the biodegradable member 30 may be contacting or coupled to one or both of the body 10 and the closure mechanism 20. The biodegradable member 30 shown prevents the closure mechanism 20 from being moved to limit the radiolucent area. The radiolucent area depicted is the hole 11. Therefore, the closure mechanism 20 is being prevented from limiting the hole 11 and restricting or preventing the therapeutic delivery of radiation by the biodegradable member 30. In various embodiments, a biodegradable member may be wedged between a body and a closure mechanism, be in contact with only a portion of the closure mechanism, interfere with a path of travel of a closure mechanism, or provide any other mechanism for at least restricting movement of a closure mechanism. When the biodegradable member 30 has eroded, degraded, or otherwise been removed, the closure mechanism 20 may cover a portion or all of the radiolucent area, as shown in FIG. 3. As shown in FIGS. 1 and 2, the biodegradable member 30 is disposed over the radiolucent area, and more specifically, the biodegradable member 30 fully covers the radiolucent area. In other embodiments, a biodegradable member may only partially cover a radiolucent area or may only extend from a body, such as the body 10, to block the path of travel of the closure mechanism. Some embodiments may include more than one biodegradable members that block the path of travel of a closure mechanism at one or more positions along a path of travel. The more than one biodegradable members may erode, degrade, or otherwise be removed at different rates such that a closure mechanism may be transitioned between different states at a particular rate.

A biodegradable member, such as the biodegradable members 30, may include any material or combination of materials that erodes, degrades, or is otherwise changed by the presence of bodily tissues or fluids. "Biodegradable" materials, as used herein, refer to any and all of bioresorbable, bioerodible, and bioabsorbable materials. "Bioresorbable" may be a more general term and refer to both bioerodible and bioabsorbable materials. "Bioerodible" may refer to a material that will erode or degrade over time due, at least in part, to contact with substances found in the surrounding tissue, fluids or by cellular action; and "bioabsorbable" may refer to a material that will be broken down and absorbed within the human body, for example, by a cell or tissue. Non-limiting examples of biodegradable materials include tissue materials, certain bioresorbable synthetic polymers, calcium phosphate, hydroxyapatite, bioactive glass, and combinations thereof. Examples of tissue materials include hard tissues, connective tissues, demineralized bone matrix and combinations thereof. Examples of bioresorbable synthetic polymers include poly (L-lactide), poly(D,L-lactide), poly(L-co-D,L-lactide), polyglycolide, poly(lactide-co-glycolide), poly(hydroxybutyrate), poly(hydroxyvalerate), tyrosine-derived polycarbonate, polyanhydride, polyorthoester, polyphosphazene, poly (dioxanone), and polyglyconate. Other similar polymers known to the art may be used and various mixtures of polymers may be combined to adjust the properties of the composition as desired.

Figure 4:
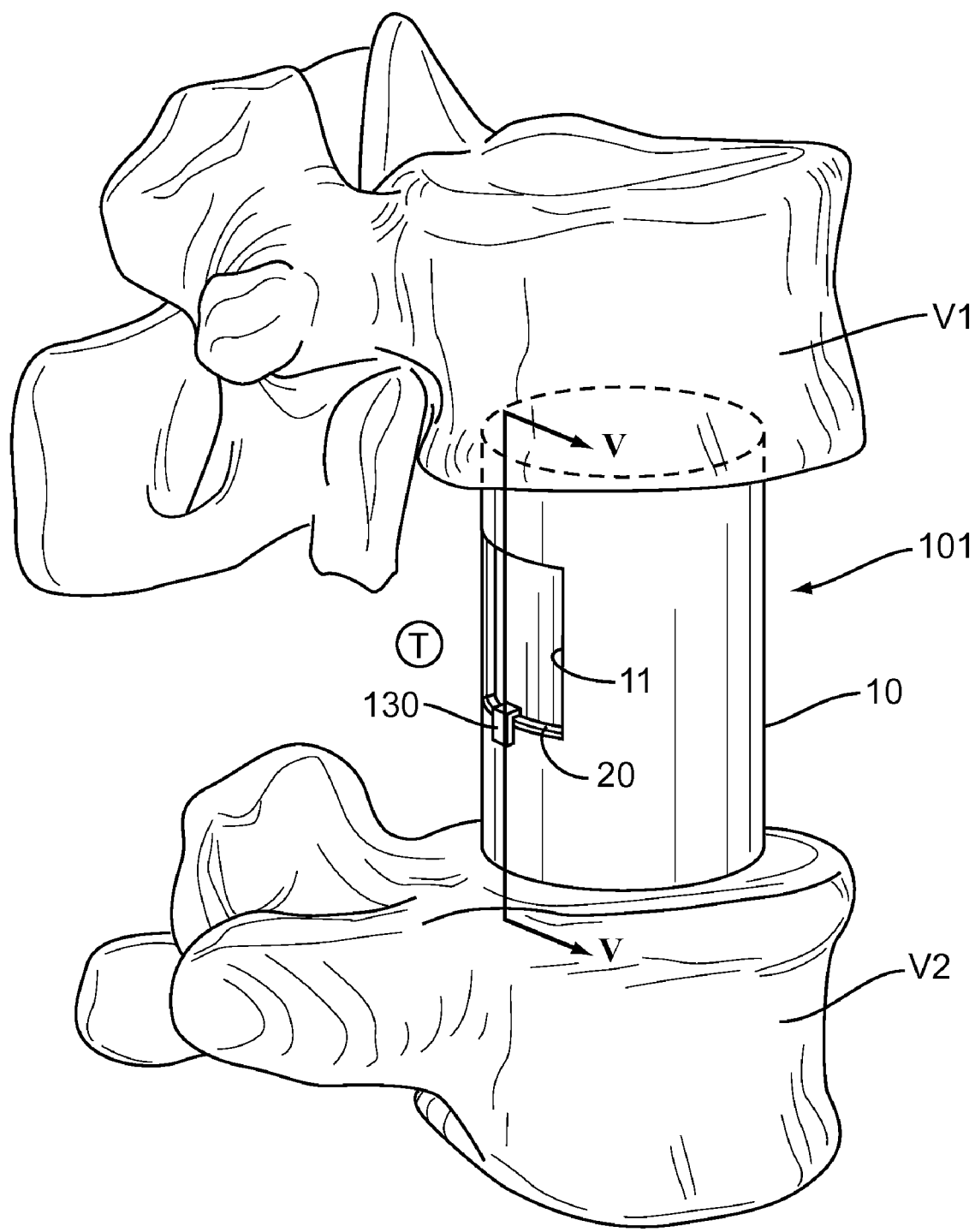
FIG. 4 is a perspective view of an embodiment of a device for therapeutically delivering radiation to tissue implanted between vertebrae.
Figure 5:
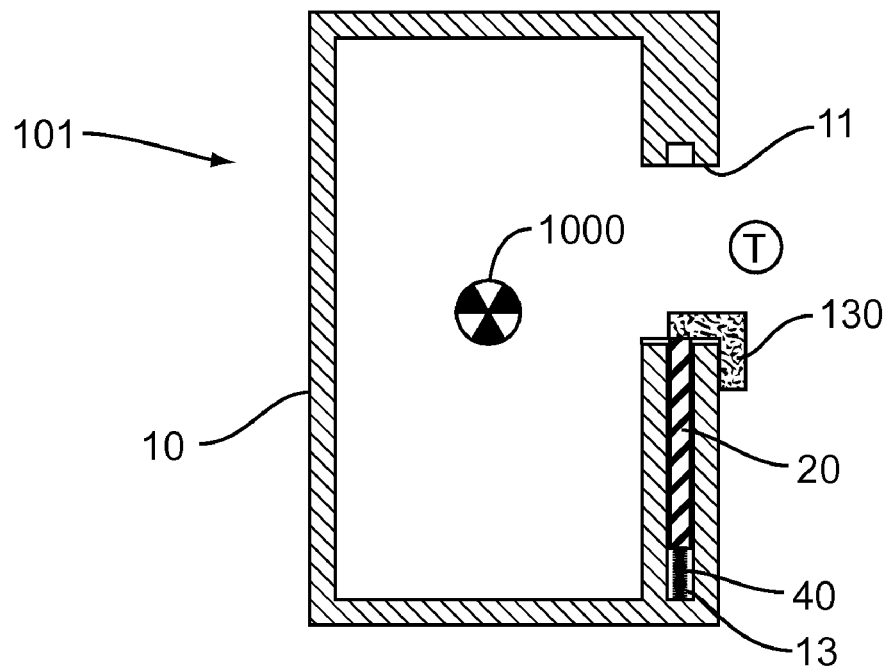
FIG. 5 is a cross-sectional view of the device of FIG. 4.
Figure 6:
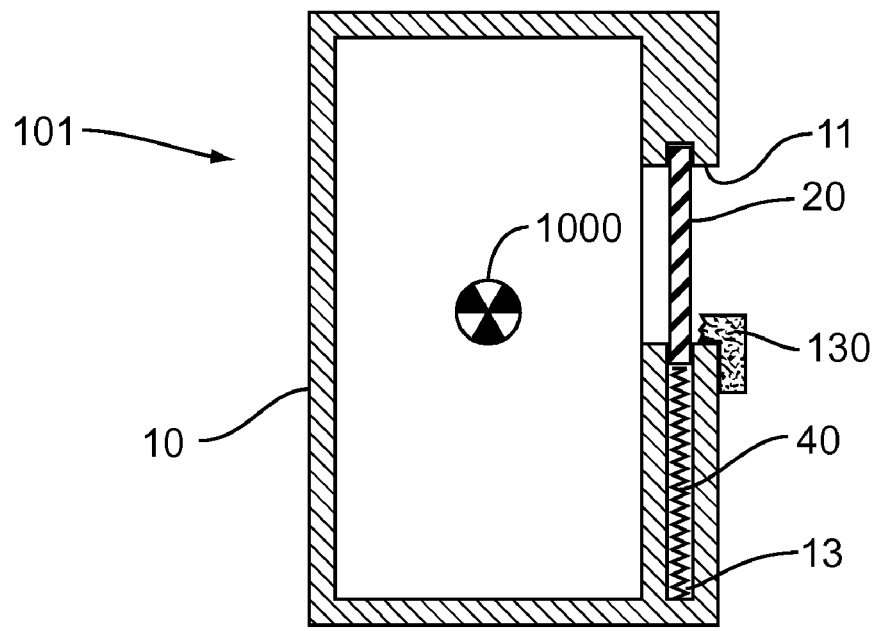
FIG. 6 is a similar cross-sectional view to the cross-sectional view of FIG. 5 in a different state of device component movement.

A device 101 for therapeutically delivering radiation to tissue is illustrated in FIGS. 4-6. The device 101 illustrated is a vertebral body replacement implant. However, in other embodiments, the device may be any implant that may be used in a space between two vertebrae, such as the illustrated first vertebra V1 and the second vertebra V2. Alternatively, the device may be a brachytherapy device or any other implantable device for delivering radiation. The lateral periphery of the device 101 is substantially round in cross-section. Other embodiments may have a periphery that is substantially the shape of an oval, kidney, triangle, rectangle, square, any polygonal or curved shape, or any combination of shapes. In some embodiments, a vertebral body replacement type device may be configured to expand from a first height of a second taller height. The device 101 or any of its component parts may be made from any biocompatible material.

The device 101 shown includes the body 10 as described herein, and as illustrated in FIGS. 1-6. The device 101 may also include the radiation source 1000 described herein, and as illustrated in FIGS. 2, 3, 5, and 6. The body 10 may include a radiolucent area, such as the hole 11. Several radiolucent area embodiments and variations are described herein.

The closure mechanism 20 made at least in part of a material that substantially blocks the transmission of radiation is also illustrated in FIGS. 4-6. The closure mechanism 20 shown is configured to cover at least a portion of the radiolucent area. In the illustrated example, radiation from the radiation emitting device 1000 is permitted to travel through the hole 11 and deliver therapeutic dosages to a treatment site "T" depicted in FIG. 5. In FIG. 6, where the hole 11 is covered by the closure mechanism 20, radiation is not permitted to be delivered laterally from the device 101. The biasing member 40 shown resides in the notch 13 in the body 10 and may include each of the features and variations describe herein.

The device 101 illustrated in FIGS. 4-6 also includes a biodegradable member 130 coupled to the body 10 and contacting the closure mechanism 20. In various embodiments, the biodegradable member 130 may be contacting or coupled to one or both of the body 10 and the closure mechanism 20. The biodegradable member 130 shown prevents the closure mechanism 20 from being moved to limit the radiolucent area. The radiolucent area depicted is the hole 11. Therefore, the closure mechanism 20 is being prevented from limiting the hole 11 and restricting or preventing the therapeutic delivery of radiation by the biodegradable member 130. In various embodiments, a biodegradable member may be wedged between a body and a closure mechanism, be in contact with only a portion of the closure mechanism, interfere with a path of travel of a closure mechanism, or provide any other mechanism for at least restricting movement of a closure mechanism. When the biodegradable member 130 has eroded, degraded, or otherwise been removed, the closure mechanism 20 may cover a portion or all of the radiolucent area, as shown in FIG. 6. The biodegradable member 130 illustrated in FIG. 6 has been eroded or weakened generally along a plane and ruptured to allow passage of the closure mechanism 20. The biodegradable member 130 only partially covers the hole 11 to block the path of travel of the closure mechanism 20. In other embodiments, a biodegradable member may be disposed over the radiolucent area, and more specifically, the biodegradable member may fully cover the radiolucent area, as illustrated in FIGS. 1 and 2.

Some embodiments of a device for therapeutically deliver radiation to tissue may include more than one biodegradable members that block the path of travel of a closure mechanism at one or more positions along a path of travel. For example, with reference to FIG. 4, biodegradable members could be provided at both lower corners of the hole 11 to provide redundant fixation. Alternatively or in addition, one or more biodegradable members could be provided at different points along the path of travel of the closure mechanism. If such biodegradable members have different rates of degradation, a progressive closure of a radiolucent area could be accomplished. In still another variation, a closure mechanism that travels over a path intersecting two or more radiolucent areas, or a closure mechanism that includes both radiolucent areas and areas that substantially block the transmission of radiation, may be released by different biodegradable members along a path to not only alter the amount of radiation emitted from a device, but to turn emission of radiation off and back on. Devices that include mechanisms that travel along a path to turn emission of radiation on and off include the devices of U.S. patent application Ser. No. 12/769,346, filed on Apr. 28, 2010, entitled, "DEVICE AND METHOD FOR DELIVERING RADIATION IN SELECTED DIRECTIONS," inventors Jonathan E. Blackwell and Keith E. Miller, Docket No. P0036012.00, which is hereby incorporated by reference in its entirety herein. The biodegradable member 130 may include any material or combination of materials that erodes, degrades, or is otherwise changed by the presence of bodily tissues, fluids, or cellular action, as further described herein with regard to the biodegradable member 30.

Any of the devices described above may be filled in whole or in part with an osteogenic material or therapeutic composition. Osteogenic materials include, without limitation, autograft, allograft, xenograft, demineralized bone, synthetic and natural bone graft substitutes, such as bioceramics and polymers, and osteoinductive factors. A separate carrier to hold materials within the device may also be used. These carriers may include collagen-based carriers, bioceramic materials, such as BIOGLASS®, hydroxyapatite and calcium phosphate compositions. The carrier material may be provided in the form of a sponge, a block, folded sheet, putty, paste, graft material or other suitable form. The osteogenic compositions may include an effective amount of a bone morphogenetic protein (BMP), transforming growth factor β1, insulin-like growth factor, platelet-derived growth factor, fibroblast growth factor, LIM mineralization protein (LMP), and combinations thereof or other therapeutic or infection resistant agents, separately or held within a suitable carrier material.

Embodiments of the invention may be applied to the lumbar spinal region, and embodiments may also be applied to the cervical or thoracic spine or between other skeletal structures. Some embodiments may also include supplemental fixation devices in addition to or as part of the devices disclosed herein to further supplement or replace spinal structures. For example, and without limitation, rod and screw fixation systems, anterior, posterior, or lateral plating systems, facet stabilization systems, spinal process stabilization systems, and any devices that supplement stabilization or replace spinal structures may be used as a part of or in combination with the devices.

The embodiments illustrated as devices 1, 101 herein, and variations to these devices may be described as a radiation source, a radiation containment means with a radiolucent area, a shutter means for closing the radiolucent area, and a release means. In particular, a radiation source may be the radiation source 1000 described herein. The radiation containment means for at least in part encapsulating the radiation source may include embodiments of the body 10 described herein with a radiolucent area such as the hole 11 or a variation as described. The shutter means for closing the radiolucent area may be any embodiment of the closure mechanism 20 or a similar mechanism. The release means for holding the shutter means in an open position to allow the delivery of therapeutically effective amounts of radiation until a degradation of the release means occurs, thereby allowing the shutter means to at least in part close and restrict the delivery of radiation may include any of the embodiments of the biodegradable members 30, 130 described herein. The release means may also include any mechanism that may be triggered, either directly or indirectly, to affect movement between the shutter means and the radiolucent containment means to close or open the shutter over the radiolucent area. In some embodiments, a biasing means is provided between the shutter means and the radiation containment means to urge the shutter means in a direction that restricts the delivery of radiation through the radiolucent area. The biasing means may include any embodiment or variation to embodiments of the biasing member 40 described herein.

An embodiment of the invention is a method of therapeutically delivering radiation to tissue. Therapeutically effective locations may include locations where a tumor or cancerous cells are present or suspected to be present, or areas from which a tumor or cancerous growth has been surgically removed. Therapeutically effective locations may also include areas where tissue growth is to be stopped or slowed, such as but not limited to, typical areas of scar tissue growth.

Some method embodiments include providing a device with a body, such as the body 10, having one or more areas comprising a material that substantially blocks the transmission of radiation. The body may include a radiolucent area, such as the hole 11. Method embodiments may also include providing a closure mechanism, such as the closure mechanism 20, made at least in part of a material that substantially blocks the transmission of radiation. The closure mechanism 20 is configured to cover all or a part of the radiolucent area. A biodegradable member, such as the biodegradable members 30, 130, is provided in some embodiments. This member may be placed between the body and the closure mechanism to restrict movement of the closure mechanism relative to the body.

Some method embodiments include implanting the body, the closure mechanism, and the biodegradable member into or near tissue to which radiation will be delivered. When a radiation source is provided with these components, then tissue may be irradiated by allowing radiation to be delivered from the body of the device at least through the radiolucent area. In some embodiments, a radiation source, such as the radiation source 1000, is inserted into the body of the device prior to implanting the body into a patient. In some embodiments, a radiation source is inserted into the body of the device after implanting the body into a patient. The radiation source or components of the radiation source may be inserted one or more of pre-operatively, inter-operatively, and post-operatively. The radiation source may be a device capable of receiving radiation or components that emit radiation and may not at all times be able to emit radiation. That is, its designation as a "radiation source" does not mean that it, or one or more of its component parts, are at all times capable of emitting radiation.

Method embodiments may also include exposing the biodegradable member to bodily fluids, tissues, or cell reactions to weaken the biodegradable member and to permit the closure mechanism to move relative to the body in a direction that restricts the delivery of radiation. Closure mechanisms of various embodiments may be moved by any effective force or mechanism. For example and without limitation, a biasing member, such as the biasing member 40, may be configured to move the closure mechanism in a direction that restricts the delivery of radiation after the biodegradable member releases the closure mechanism in a direction that restricts the delivery of radiation. Other example forces include physical, magnetic, electrical, or any effective force applied to devices directly or to actuators or control mechanism that ultimately act on the closure mechanism to move the closure mechanism relative to the body of a device.

Embodiments of the device for therapeutically delivering radiation may be implanted from any surgical approach, for example to the spine, including but not limited to, posterior, lateral, anterior, transpedicular, lateral extracavitary, in conjunction with a laminectomy, in conjunction with a costotransversectomy, or by any combination of these and other approaches. Similarly, approaches from any effective direction may be made to any part of the anatomy for delivering brachytherapy or radiation for any other purpose.

Various method embodiments of the invention are described herein with reference to particular devices. However, in some circumstances, each disclosed method embodiment may be applicable to each of the devices, or to some other device operable as disclosed with regard to the various method embodiments.

Terms such as anterior, posterior, lateral, within, inside, outside, lower, upward, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A device for therapeutically delivering radiation to tissue comprising:
    a body having one or more areas comprising a material that substantially blocks the transmission of radiation;
    a radiation source located within the body and configured to deliver radiation;
    a radiolucent area in the body;
    a closure mechanism made at least in part of a material that substantially blocks the transmission of radiation and that is configured to cover at least a portion of the radiolucent area; and
    a biodegradable member coupled to the body and contacting the closure mechanism to prevent the closure mechanism from being moved to limit the radiolucent area and thereby restrict or prevent the therapeutic delivery of radiation.

2. The device of claim 1 wherein the device is at least a portion of a vertebral body replacement implant.

3. The device of claim 1 wherein the radiolucent area of the body is an area where material has been removed to provide one or more openings.

4. The device of claim 1 wherein the radiolucent area of the body is a closed area comprising radiolucent material.

5. The device of claim 1, further comprising a biasing member disposed between the body and the closure mechanism to urge the closure mechanism in a direction that restricts the delivery of radiation through the radiolucent area.

6. The device of claim 1 wherein the biodegradable member is disposed at least in part over the radiolucent area.

7. The device of claim 1 wherein the biodegradable member fully covers the radiolucent area.

8. The device of claim 1 wherein the biodegradable member includes one or more tabs that block a path of travel of the closure mechanism until the one or more tabs are biodegraded sufficiently to be moved from the path of travel.

9. The device of claim 1 wherein the biodegradable member is wedged between the body and the closure mechanism to block a path of travel of the closure mechanism until the biodegradable member is biodegraded sufficiently to be moved from the path of travel.

10. The device of claim 1 wherein the biodegradable member comprises a bioresorbable polymer.

11. A device for therapeutically delivering radiation to tissue comprising:
    a radiation source;
    a radiation containment means comprising a material that substantially blocks the transmission of radiation, the radiation containment means for at least in part encapsulating the radiation source;
    a radiolucent area in the radiation containment means;
    a shutter means for closing the radiolucent area, wherein the shutter means is made at least in part of a material that substantially blocks the transmission of radiation; and
    a release means coupled to the radiation containment means and contacting the shutter means, the release means for holding the shutter means in an open position to allow the delivery of therapeutically effective amounts of radiation until a degradation of the release means occurs, thereby allowing the shutter means to at least in part close and restrict the delivery of radiation.

12. The device of claim 11, further comprising a biasing means for urging the shutter means in a direction that restricts the delivery of radiation through the radiolucent area.

13. The device of claim 11 wherein the radiolucent area in the radiation containment means is an area where material has been removed to provide one or more openings.

14. The device of claim 11 wherein the radiolucent area in the radiation containment means is a closed area comprising radiolucent material.

15. The device of claim 11 wherein the release means includes a biodegradable material.

16. The device of claim 15 wherein the biodegradable material includes a bioresorbable polymer.

17. A method of therapeutically delivering radiation to tissue comprising:
    providing a device with a body having one or more areas comprising a material that substantially blocks the transmission of radiation, and wherein the body includes a radiolucent area;
    providing a closure mechanism made at least in part of a material that substantially blocks the transmission of radiation, wherein the closure mechanism is configured to cover the radiolucent area;
    providing a biodegradable member between the body and the closure mechanism to restrict movement of the closure mechanism relative to the body;
    implanting the body, the closure mechanism, and the biodegradable member into or near tissue to which radiation will be delivered;
    irradiating the tissue by allowing radiation to be delivered from the body at least through the radiolucent area; and
    exposing the biodegradable member to bodily fluids, tissues, or cell reactions to weaken the biodegradable member and to permit the closure mechanism to move relative to the body in a direction that restricts the delivery of radiation.

18. The method of claim 17, further comprising providing a biasing member to urge the closure mechanism in a direction that restricts the delivery of radiation, and wherein exposing the biodegradable member to bodily fluids, tissues, or cell reactions to weaken the biodegradable member permits the biasing member to move the closure mechanism in a direction that restricts the delivery of radiation.

19. The method of claim 18, further comprising inserting a radiation source into the body after implanting the body.

20. The method of claim 17, further comprising inserting a radiation source into the body prior to implanting the body.

* * * * *